United States Patent
Kim (10) Patent No.: US 12,385,814 B2
(45) Date of Patent: Aug. 12, 2025

(54) METHOD AND APPARATUS FOR CELL STAINING WITHOUT CELL LOSS

(71) Applicant: DAEGU GYEONGBUK INSTITUTE OF SCIENCE AND TECHNOLOGY, Daegu (KR)

(72) Inventor: Min Seok Kim, Daegu (KR)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 348 days.

(21) Appl. No.: 17/207,890

(22) Filed: Mar. 22, 2021

(65) Prior Publication Data

US 2021/0302284 A1    Sep. 30, 2021

(30) Foreign Application Priority Data

Mar. 24, 2020   (KR) .................. 10-2020-0035418

(51) Int. Cl.
G01N 1/30 (2006.01)
C12N 11/087 (2020.01)
G01N 1/31 (2006.01)

(52) U.S. Cl.
CPC ............. *G01N 1/30* (2013.01); *C12N 11/087* (2020.01); *G01N 1/31* (2013.01); *G01N 2001/302* (2013.01); *G01N 2001/305* (2013.01)

(58) Field of Classification Search
CPC ...... G01N 1/30; G01N 1/31; G01N 2001/302; G01N 2001/305; G01N 2001/2846; C12N 11/087
See application file for complete search history.

(56) References Cited

U.S. PATENT DOCUMENTS

2021/0239683 A1*  8/2021  Ma .......................... C08J 3/075

FOREIGN PATENT DOCUMENTS

| CA | 2637663 C * | 6/2015 | ............ C12M 21/08 |
|---|---|---|---|
| KR | 10-2012-0090039 A | 8/2012 | |
| KR | 10-1290648 B1 | 7/2013 | |
| KR | 10-2016-0034541 A | 3/2016 | |
| KR | 10-2019-0033883 A | 4/2019 | |

OTHER PUBLICATIONS

T. Andersen, C. Markussen, M. Dornish, et al.; "In Situ Gelation for Cell Immobilization and Culture in Alginate Foam Scaffolds;" Mary Ann Liebert, Inc.; Tissue Engineering: Part A vol. 20, pp. 600-610, 2014.

S. Caliari and J. Burdick; "A Practical Guide to Hydrogels for Cell Culture;" Department of Bioengineering, University of Pennsylvania; published in Nat Methods 13 (5), pp. 405-414, 2016.

Y. Wan, M. Winter, B. Delalat, et al.; "Nanostructured Polystyrene Well Plates Allow Unbiased High-Throughput Characterization of Circulating Tumour Cells;" ACS Applied Materials & Interfaces; published by the American Chemical Society, 2014.

Office Action from corresponding Korean Patent Application No. 10-2020-035418, dated Jul. 29, 2021.

* cited by examiner

*Primary Examiner* — Blaine Lankford
(74) *Attorney, Agent, or Firm* — Sughrue Mion, PLLC (57) ABSTRACT

Provided is a method and apparatus for cell staining without cell loss, and more particularly, to a method and apparatus for cell staining without cell loss during treatment of a staining reagent or washing reagent by immobilizing cells to be analyzed in a phase change material before staining. A method for cell staining without cell loss may effectively prevent cell loss during staining and analysis of rare cells that are becoming important in clinical diagnosis, and thus may facilitate observation, analysis and diagnosis thereby even with a trace amount of sample. In addition, as the method for cell staining without cell loss allows immobilization of cells, it makes discrimination and isolation of single cells easy, and may be effectively used in analysis of the isolated cells.

8 Claims, 11 Drawing Sheets

METHOD AND APPARATUS FOR CELL STAINING WITHOUT CELL LOSS

CROSS-REFERENCE TO RELATED APPLICATION

This application claims priority to and the benefit of Korean Patent Application No. 10-2020-0035418, filed on Mar. 24, 2020, the disclosure of which is incorporated herein by reference in its entirety.

FIELD

The present disclosure describes a method and apparatus for cell staining without cell loss, and more particularly, describes a method and apparatus for cell staining without cell loss during treatment of a staining reagent or washing reagent by immobilizing cells to be analyzed in a phase change material before staining.

BACKGROUND

Immunocytochemistry (ICC) staining is a technique that that is widely used to observe the location and shape of a specific protein or cells using an antibody specifically binding thereto. In the field of clinical diagnosis, a step of specifically staining a material or cells to be analyzed is an important step for not only verifying and observing the presence thereof, but also diagnosing and analyzing a disease using the same.

Particularly, to stain suspension cells, primarily, a step of localizing cells on the bottom surface of an observation slide is important. Conventional pretreatment methods for cell staining include, representatively, a cytospin method in which a sample is isolated and localized using centrifugation and then stained, and a smear method in which a sample to be observed is widely spread on a slide glass, dried and then stained. In addition, recently, Curiox has also developed a new cell pretreatment method that does not require centrifugation.

However, in the conventional cell pretreatment methods, there was a disadvantage that 30% or more of cells in a sample are lost during the treatment of a staining reagent and washing. Cells that are easy to secure large amounts of samples, such as a commercialized cell line or immune cells have no problems in analysis and diagnosis despite cell loss, whereas in the case of rare cells that are present in a very small amount in a sample, such as circulating tumor cells (CTCs) or fetal cells, during the pretreatment process, such cell loss may cause critical problems in analysis and diagnosis, and also make analysis of a sample that is difficult to obtain impossible.

However, until now, few cell staining methods that can prevent cell loss from a sample have been developed. Recently, one paper reported that cell loss may be reduced by immobilizing cells to be analyzed on a membrane surface through plasma treatment (ACS. Appl. Master. Interfaces 2014, 6, 20828-20836). However, this method not only requires expensive equipment, but also has a problem in that reproducibility is remarkably low depending on a cell type and a charge value, and therefore, it is impossible to commercialize.

Accordingly, the inventors have made great effect to develop a method for cell staining without cell loss, which is easy to commercialize regardless of the type of cells, resulting in the completion of the present disclosure.

SUMMARY

The present disclosure provides a method for cell staining without cell loss, which includes: (a) inputting a phase change material and a biosample containing cells to be analyzed into a chamber; (b) localizing the cells to be analyzed, which are suspended in the sample, on the bottom surface of the chamber; (c) immobilizing the cells on the bottom surface by solidifying the phase change material; and (d) staining the immobilized cells.

The present disclosure provides an apparatus for cell staining without cell loss, which includes: a chamber unit 100 whose top surface is open; a bezel unit 200 which is installed in the chamber unit 100 and has open top and bottom surfaces; and a thickness adjustment unit 300 which is installed in the bezel unit 200 and spaced a predetermined distance apart from the bottom surface of the chamber unit 100.

The present disclosure provides a method for analyzing a single cell, which includes: (a) inputting a phase change material and a biosample containing cells to be analyzed into a chamber; (b) localizing the cells to be analyzed, which are suspended in the sample, on the bottom surface of the chamber; (c) immobilizing the cells on the bottom surface by solidifying the phase change material; (d) staining the immobilized cells; and (e) isolating the stained cells.

To solve the above-described problems, the present disclosure provides a method for cell staining method without cell loss which may prevent cell loss during staining and washing by immobilizing cells to be analyzed in a sample on the bottom of a staining apparatus, and a staining apparatus for this method.

Specifically, the present disclosure provides a method for cell staining without cell loss, which includes: (a) inputting a phase change material and a biosample containing cells to be analyzed into a chamber; (b) localizing the cells to be analyzed, which are suspended in the sample, on the bottom surface of the chamber; (c) immobilizing the cells on the bottom surface by solidifying the phase change material; and (d) staining the immobilized cells.

In the step (a) of the present disclosure, the phase change material and the biosample may be input simultaneously, in combination or independently, and the order of input is not limited.

Preferably, in the present disclosure, the step (a) may include: inputting a phase change material into a chamber of a sample staining apparatus; installing a bezel unit for gel stabilization in the chamber; and inputting a biosample containing the cells to be analyzed.

The term "phase change material" used herein refers to a material whose phase is changed by UV or temperature. Particularly, in one embodiment of the present disclosure, the phase change material may include a photocurable or heat-curable hydrogel, but the present disclosure is not limited thereto. The photocurable hydrogel is a material that can transition to a solid or gel state from a liquid or sol state when a specific wavelength of light such as UV is applied for a predetermined time. The heat-curable hydrogel is a material that can phase-transition by a temperature change, and a material that is present in a liquid or sol state at room temperature, but can transition to a solid or gel state at specific temperature or more.

According to one embodiment of the present disclosure, the phase change material may include polyethylene glycol (PEG) acrylate derivatives, PEG methacrylate derivatives, polyvinyl alcohol (PVA) derivatives, hyaluronic acid derivatives, dextran methacrylate, poly(N-isopropylacrylamide)

(pNiPAAm), polyethylene glycol (PEG), poly(propylene glycol) (PPG), poly(methacrylic acid) (PMAA), methylcellulose (MC), chitosan, and poloxamers, and preferably, the phase change material may include poly ethylene glycol diacrylate (PEGDA).

According to one embodiment of the present disclosure, the biosample may include a cell sample, a cell culture medium, a tissue extract, cancer tissue, serum, plasma, saliva, tears, sweat, urine, feces, a cerebrospinal fluid (CSF), ascites, an amniotic fluid, semen, and milk, and there is no limitation as long as it is well known to those of ordinary skill in the art as a biosample for cell analysis.

According to one embodiment of the present disclosure, the method of localizing cells in a sample on the bottom surface in the step (b) preferably uses a centrifugal force, but there is no limitation as long as it is a method well known to those of ordinary skill in the art.

According to one embodiment of the present disclosure, the method may further include additionally installing a unit that can adjust the thickness of a phase change material after the step (b), and removing the thickness adjustment unit after the step (c).

The present disclosure also provides an apparatus for cell staining without cell loss, which includes: a chamber unit 100 whose top surface is open; and a bezel unit 200 which is installed in the chamber unit 100 and has open top and bottom surfaces.

According to one embodiment of the present disclosure, the apparatus for cell staining without cell loss may further include a thickness adjustment unit 300 installed in the bezel unit 200.

According to one embodiment of the present disclosure, the bottom surface of the chamber unit 100 may be formed flat or formed with a plurality of microwells 110.

According to one embodiment of the present disclosure, a groove having a predetermined shape may be formed in a part or all of the lower end of the side surface of the bezel unit 200. Here, the groove in the predetermined shape may have a "¬"-shaped, triangle-shaped or wedge-shaped cross-section.

According to one embodiment of the present disclosure, the thickness adjustment unit 300 may have a passage 310 through which a fluid can flow in the bottom or side surface.

The present disclosure also provides a method for analyzing a single cell, which includes: (a) inputting a phase change material and a biosample containing cells to be analyzed into a chamber; (b) localizing the cells to be analyzed, which are suspended in the sample, on the bottom surface of the chamber; (c) immobilizing the cells on the bottom surface by solidifying the phase change material; (d) staining the immobilized cells; and (e) isolating the stained cells.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Hereinafter, embodiments will be described in detail with reference to exemplary drawings. It should be noted that, when reference numerals are assigned to components of each drawing, like components are denoted by the same reference numerals, even if they are represented on other drawings. In addition, in description of embodiments of the present disclosure, detailed descriptions of known configurations or functions related thereto will be omitted when it is determined that the detailed descriptions would hinder the understanding of embodiments of the present disclosure.

A component included in any one embodiment and a component having a common function will be described using the same name in another embodiment. Unless stated otherwise, the description in any one embodiment may be applied to another embodiment, and detailed description in the overlapping range will be omitted.

Figure 1:
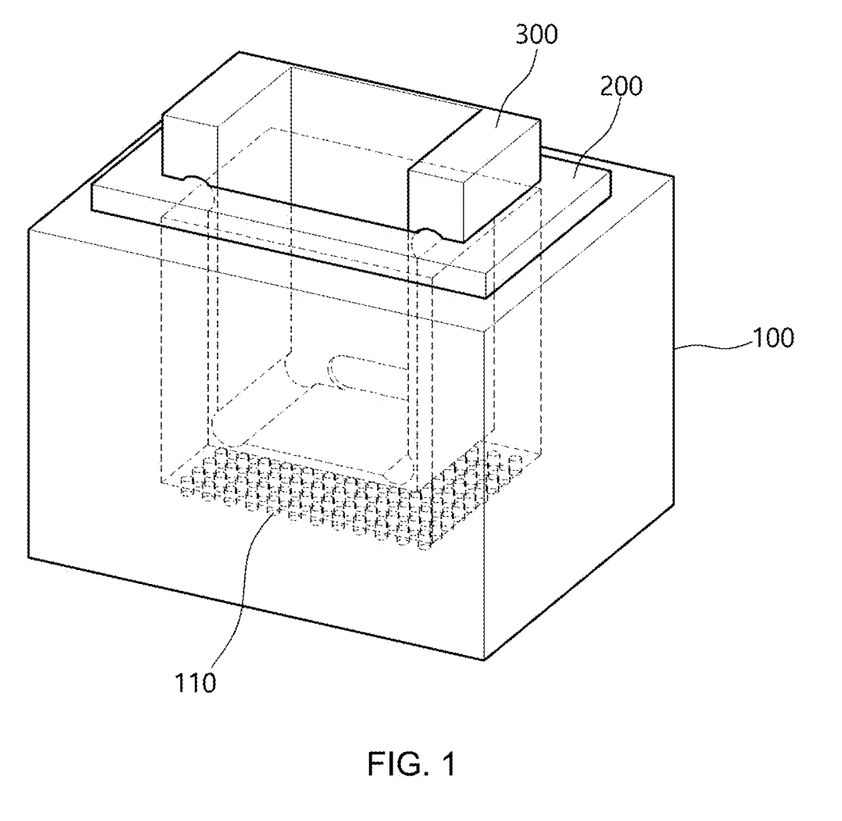
FIGS. 1, 2 and 3 are schematic diagrams of a cell staining apparatus according to one embodiment of the present disclosure.
Figure 2:
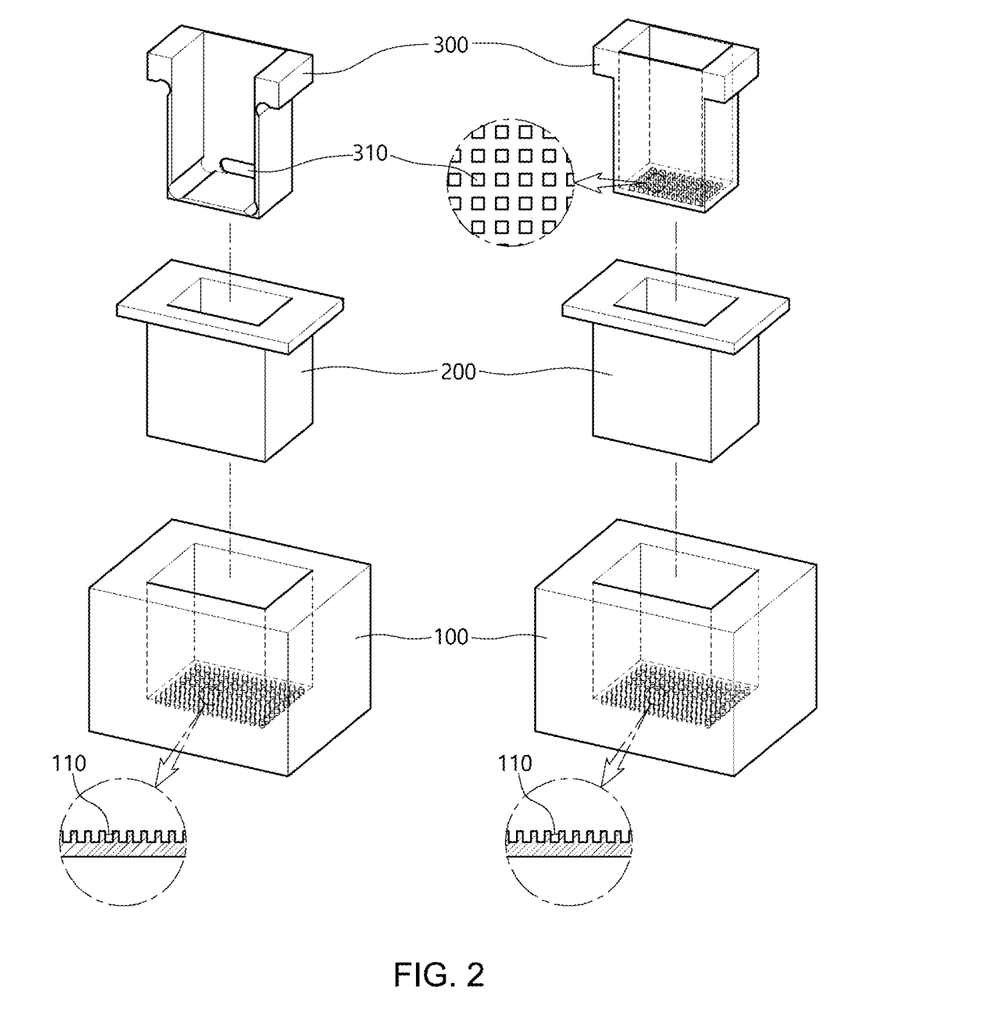
Figure 3:
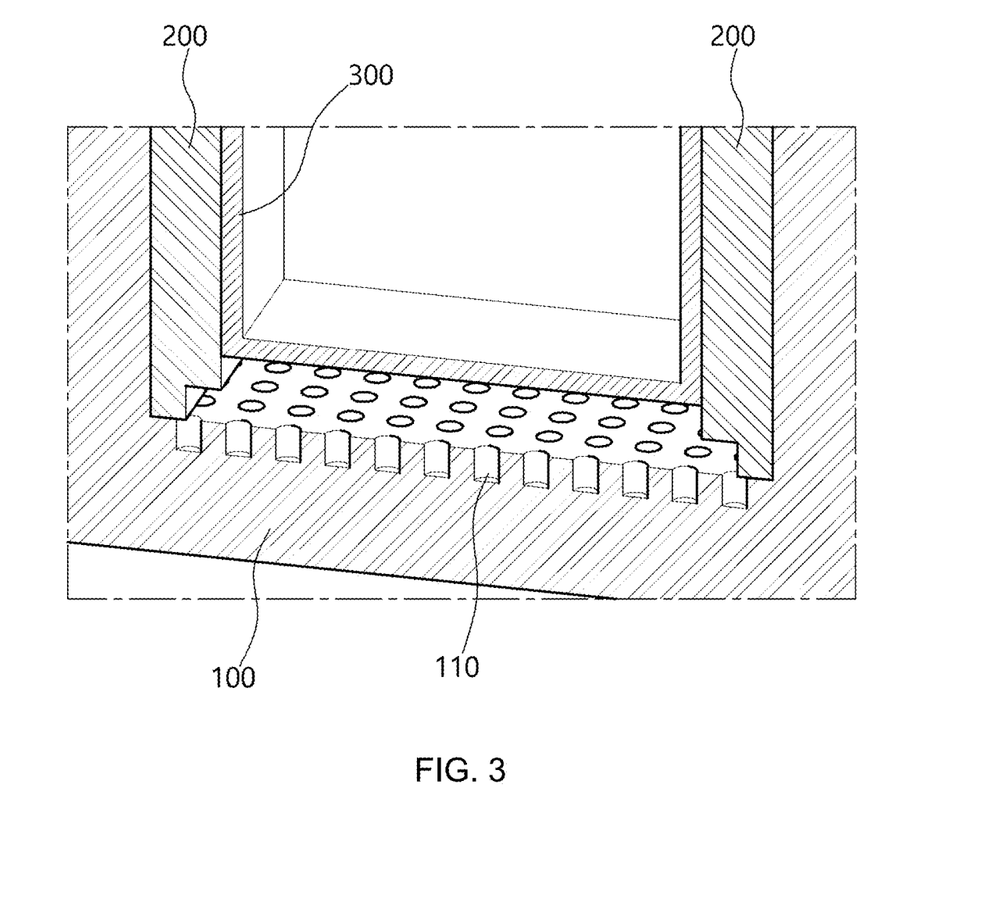

FIGS. 1 to 3 are schematic diagrams of a cell staining apparatus according to one embodiment of the present disclosure.

Referring to FIG. 1, the cell staining apparatus according to one embodiment of the present disclosure may include a chamber unit 100 and a bezel unit 200.

Here, the cell staining apparatus according to one embodiment of the present disclosure is for detecting and analyzing the presence of cells by staining the same in a sample with a cell-specific staining reagent. Hereinafter, a case where the sample is a blood sample and the cells to be analyzed are circulating tumor cells (CTCs) will be described.

According to one embodiment of the present disclosure, the chamber unit 100 may include an open top for inputting a sample to be analyzed and a phase change material.

A material of the chamber unit 100 may be selected in consideration of the step of solidifying the phase change material, and is not limited to a specific material as long as the solidifying step is not inhibited. Particularly, according to one embodiment of the present disclosure, when a photocurable material is used as the phase change material, the photocurable material should be a material through which light with a specific wavelength can pass, and when a heat-curable material is used as the phase change material, it should be a material capable of achieving a desired temperature. However, the present disclosure is not limited to a particular material as long as the phase change step is not inhibited.

In one embodiment of the present disclosure, to facilitate visualization and analysis after cell staining, the bottom surface is formed in a square shape, but the shape is not limited according to a user's convenience.

The chamber unit 100 of the present disclosure serves as a plate for observation and analysis after a material to be analyzed is immobilized on the bottom surface thereof. Particularly, referring to FIGS. 1 to 3, the chamber unit 100 may have a bottom surface which is formed flat or on which a plurality of microwells 110 are formed.

The size of the microwell 110 may be 1 to 50 µm, preferably, 20 to 40 µm, and more preferably, 30 µm according to the size of cells to be analyzed.

When a blood sample containing CTCs is injected through the open top of the chamber unit 100, an individual CTC may enter each microwell, and therefore, observation and analysis of each cell may be facilitated.

The bezel unit 200 may be installed in the chamber unit 100.

The bezel unit 200 of the present disclosure has open top and bottom surfaces, and when the phase change material input into the chamber unit 100 is solidified on the bottom surface, thereby forming a thin polymer gel with a thickness of 1 mm or less, it may serve to stabilize a gel shape. Specifically, as a part or all of the lower end of the side surface of the bezel unit 200 is in contact with the bottom surface of the chamber unit 100, by uniformly fixing corners of the solidified gel on the bottom surface of the chamber unit 100, it is possible to effectively prevent the gel from being skewed to one side, deformed or separated from the bottom surface and folded (see FIG. 5).

Particularly, as shown in FIG. 3, the bezel unit 200 may include a groove having a predetermined shape in a part or all of a lower end of the side surface thereof. The cross-section of the groove formed at the end may be formed in the shape of "¬," a triangle with one oblique side, or a wedge with two oblique sides. The groove may serve to prevent cell attachment to an inner side wall of the bezel unit 200, and may be formed in the entirety or a part of the lower end of the side surface of the bezel unit 200.

In one embodiment of the present disclosure, a thickness adjustment unit 300 may be further installed in the bezel unit 200.

The thickness adjustment unit 300 of the present disclosure may be spaced a predetermined distance from the bottom surface of the chamber unit 100. According to the distance between the thickness adjustment unit 300 and the bottom surface of the chamber unit 100, the thickness of the solidified phase change material may be adjusted for the purpose of an experiment. Specifically, according to one embodiment of the present disclosure, when the thickness adjustment unit 300 is installed at an interval of 200 µm from the bottom surface of the chamber unit 100, a polymer gel with a thickness of 200 µm may be formed under conditions of solidifying the phase change material.

The bottom surface of the thickness adjustment unit 300 may be completely closed or partially open. To control the solidification thickness of the phase change material formed under the thickness adjustment unit 300, the bottom surface of the thickness adjustment unit 300 may be formed with a material/shape that can effectively block light or heat according to the phase change condition of the phase change material. Particularly, according to one embodiment of the present disclosure, when a photocurable hydrogel is input as the phase change material, UV may be blocked due to the material and/or shape of the bottom surface of the thickness adjustment unit 300, and thus a phase change may occur only at the lower end of the bottom surface of the thickness adjustment unit 300.

The installation of the thickness adjustment unit 300 may be determined according to the type and properties of the used phase change material. For example, when a heat-curable phase change material which is easily adjusted in thickness during a phase change is used, a solidification thickness may be controlled by adjusting temperature and/or time when heat required for solidification is applied from the bottom surface of the chamber unit 100. In this case, the thickness adjustment apparatus 300 may not be necessarily included.

Particularly, referring to FIG. 2, the thickness adjustment unit 300 may have a passage 310 through which a fluid can flow in the bottom or side surface. Among the phase change material and the biosample input into the chamber unit 100, a remaining fluid except cells to be immobilized on the bottom surface of the chamber unit 100 and a certain amount of phase change material may pass through the passage 310 formed in the thickness adjustment unit 300.

The passage 310 may be formed by opening a part or all of a side surface of the thickness adjustment unit 300.

In addition, the passage 310 may be formed by forming a mesh in the bottom surface of the thickness adjustment unit 300. Specifically, when the passage 310 is formed in the bottom surface, the ratio and size of an open part and a closed part may be adjusted so that the function of adjusting the thickness of a phase change material is not inhibited due to the open part. Preferably, the interval of the mesh formed in the bottom surface of the thickness adjustment unit 300 may be approximately 1 mm.

Figure 4:
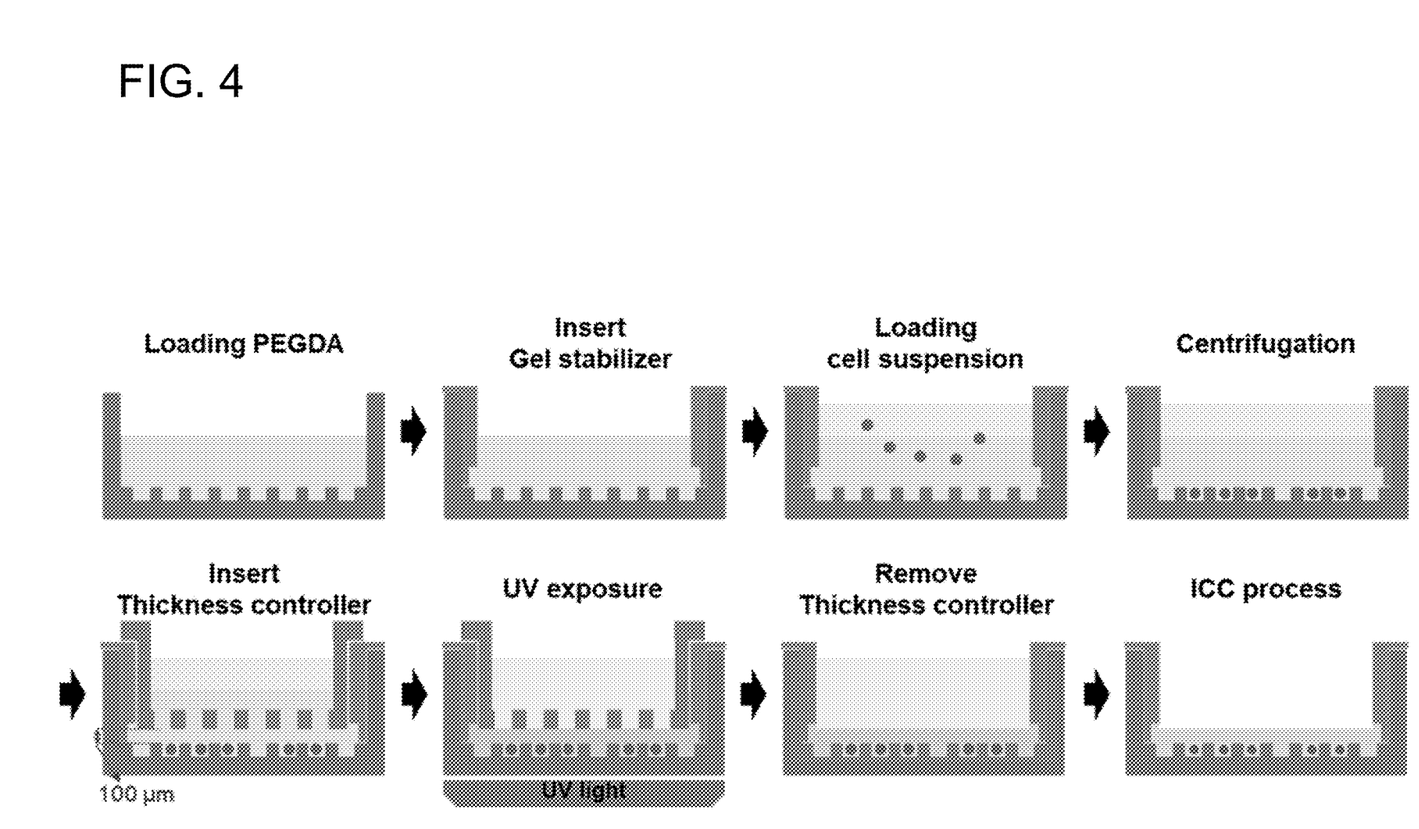
FIG. 4 shows a method for cell staining without cell loss according to one embodiment of the present disclosure step by step.

FIG. 4 shows a method for cell staining without cell loss according to one embodiment of the present disclosure step by step.

Hereinafter, the method will be described with a blood sample as a biosample, and CTCs as cells to be analyzed, and as a phase change material, a type of photocurable hydrogel, poly ethylene glycol diacrylate (PEGDA) is used.

First, in the method of the present disclosure, a phase change material and a biosample containing cells to be analyzed are input into a chamber for cell staining.

According to one embodiment of the present disclosure, the phase change material may be a photocurable or heat-curable hydrogel. Preferably, the phase change material of the present disclosure may include polyethylene glycol (PEG) acrylate derivatives, PEG methacrylate derivatives, polyvinyl alcohol (PVA) derivatives, hyaluronic acid derivatives, dextran methacrylate, poly(N-isopropylacrylamide) (pNiPAAm), polyethylene glycol (PEG), poly(propylene glycol) (PPG), poly(methacrylic acid) (PMAA), methylcellulose (MC), chitosan, and poloxamers.

According to one embodiment of the present disclosure, PEGDA, as a phase change material, is first input, and then a biosample is input.

Here, to maintain the shape of a thin polymer gel formed after PEGDA is solidified, a step of installing a bezel unit (gel stabilizer) in the chamber may be further included. The bezel unit may be installed before or after inputting the phase change material and/or biosample.

Subsequently, the cells to be analyzed, which are suspended in the sample, are placed on the bottom surface of the chamber.

A trace amount of the CTCs to be analyzed are contained in the blood sample, and a centrifugation method may be used to separate them from other materials and the fluid in the sample and place them on the bottom surface of the chamber.

Subsequently, the cells are immobilized on the bottom surface by solidifying the phase change material.

The PEGDA used in one embodiment of the present disclosure is a material in which a phase change from a sol or liquid state to a gel or solid state occurs by UV irradiation. By UV irradiation to the lower part of the chamber, PEGDA may be solidified from the bottom surface of the chamber, and accordingly the CTCs attached to the bottom surface of the chamber may be immobilized while contained in the phase change material.

Here, before UV irradiation to the phase change material, a thickness adjustment apparatus may be installed in the chamber or bezel. Since the thickness adjustment apparatus may be installed by being spaced a predetermined distance from the bottom surface of the chamber according to a desired thickness of the phase change material, the thickness of the solidified phase change material may be freely adjusted.

While the thickness adjustment apparatus is installed, a desired thickness of gel is formed by UV irradiation, and then the thickness adjustment apparatus is removed.

Afterward, the cells are stained by treating the gel in which the cells are immobilized with a cell staining reagent and a washing reagent.

To stain cells by a conventional immunocytochemical (ICC) method, during the process of inputting and washing a reagent via several steps, the cells to be analyzed are also washed away, but cell loss may be completely prevented by staining the cells immobilized in the gel according to the present disclosure.

Figure 10:
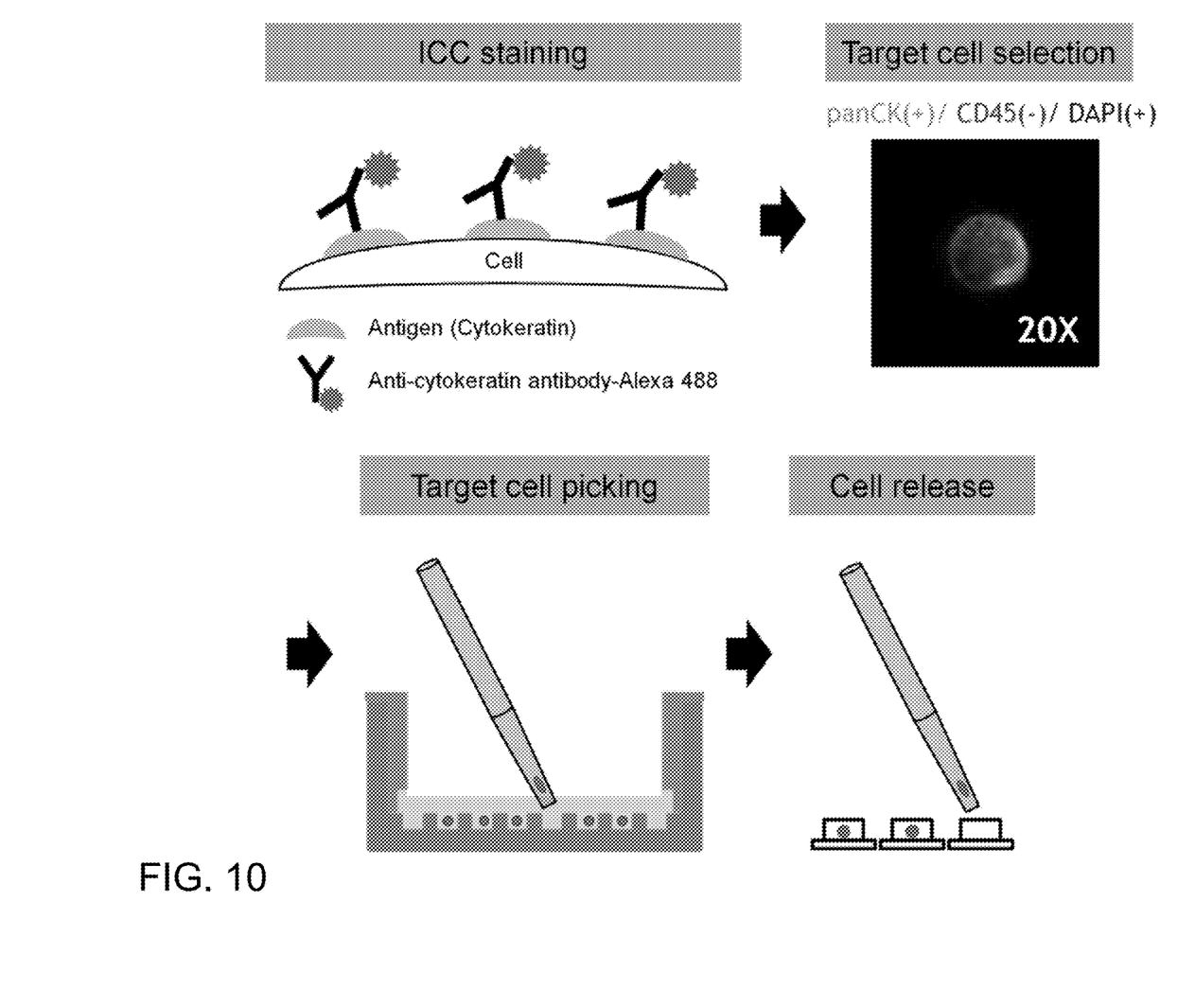
FIG. 10 shows a process of single cell isolation according to one embodiment of the present disclosure step by step.

FIG. 10 shows a process of single cell isolation according to one embodiment of the present disclosure step by step.

First, for single cell analysis, according to the method for cell staining without cell loss, cells to be analyzed are immobilized in a phase change material, and then subjected to ICC. The desired cells to be analyzed may be selected through observation and analysis after cell staining. Accordingly, the selected target cells are isolated one by one.

EXAMPLE

Hereinafter, the present disclosure will be described in more detail with reference to examples. The examples are merely provided to more fully describe the present disclosure, and it will be obvious to those of ordinary skill in the art that the scope of the present disclosure is not limited to the following examples.

Example 1. Change in Gel Thickness According to the Presence or Absence of Bezel Unit or Thickness Adjustment Unit To confirm an effect caused by the presence or absence of a bezel unit and a thickness adjustment unit in an apparatus for cell staining without cell loss (microwell array chip) of the present disclosure, an experiment was conducted as follows.

Figure 5:
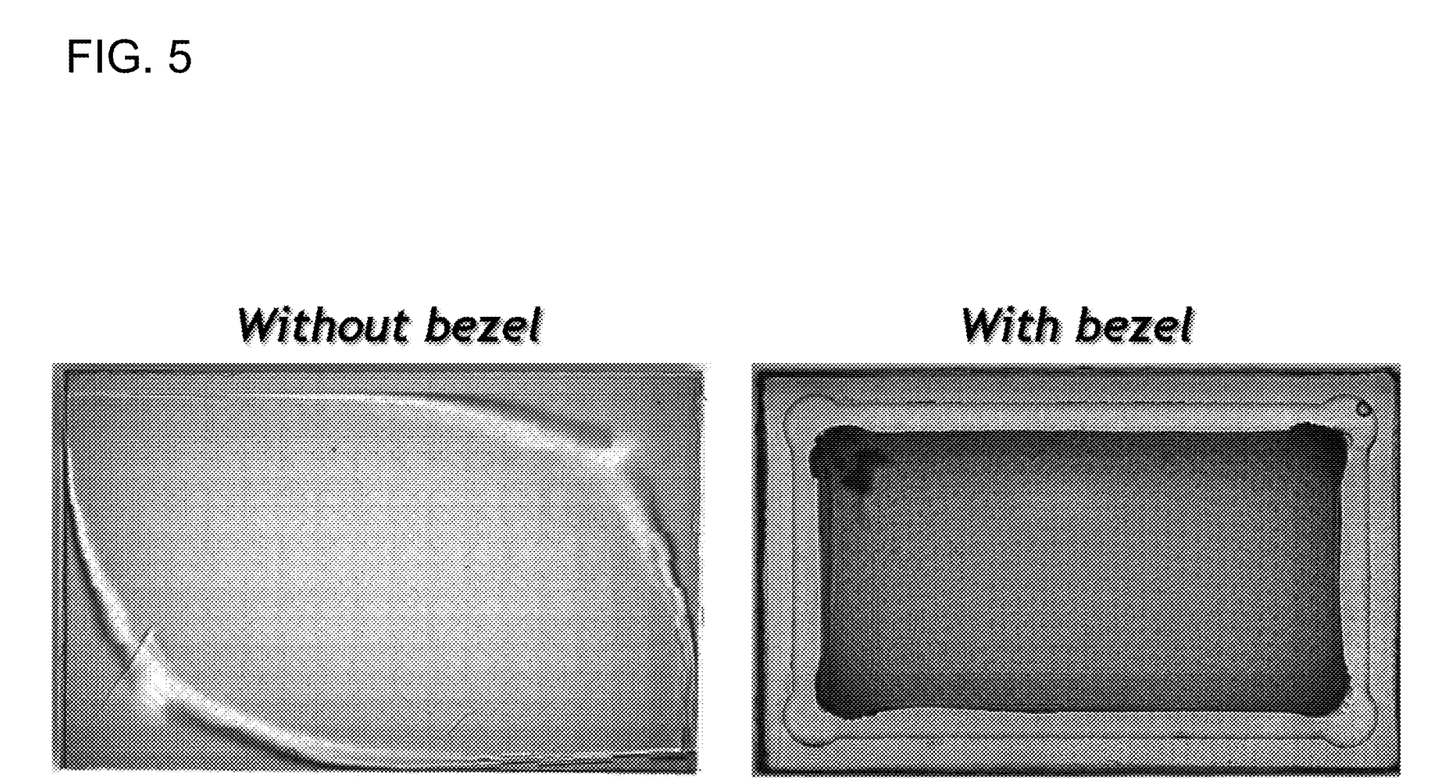
FIG. 5 shows an effect according to the use of a bezel unit of the present disclosure.

First, to minimize the loss of rare cells to be observed through ICC, a PEGDA gel was formed as thin as possible, and the shapes of the solidified PEGDA gel according to the presence or absence of a bezel unit were compared. As a result, as shown in FIG. 5, when the PEGDA was solidified (gelation) without installation of a bezel unit, during the gelation, the PEGDA film was separated from a microwell array, and when the bezel unit was installed and then solidified, it was confirmed that the PEGDA film was formed while binding well to the microwell array.

Figure 6:
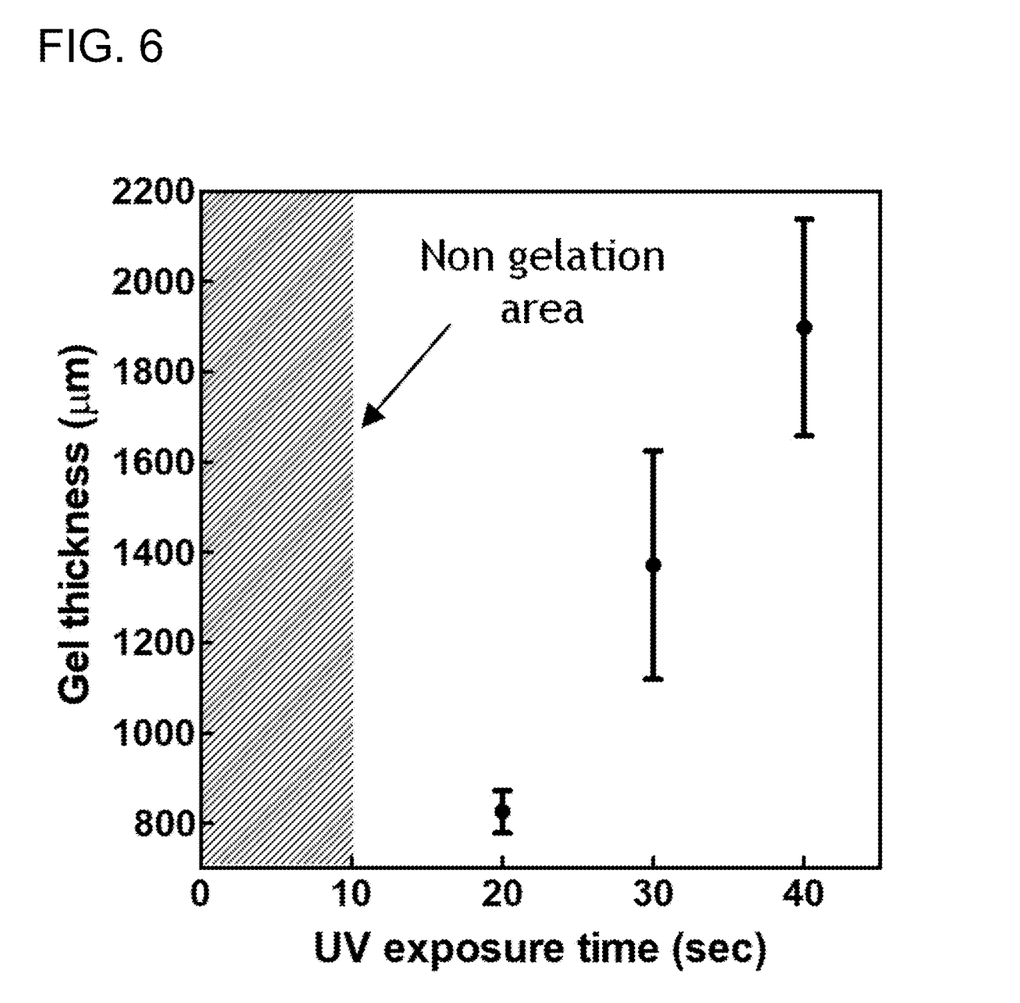
FIG. 6 shows the thickness of a hydrogel according to UV exposure time when a thickness adjustment unit is not used.

Here, the gel thickness may vary according to UV exposure time of the PEGDA. It can be confirmed that the gel thickness increases over the time for applying UV, and when exposed to UV for less than 10 seconds, gelation does not proceed (FIG. 6).

Figure 7:
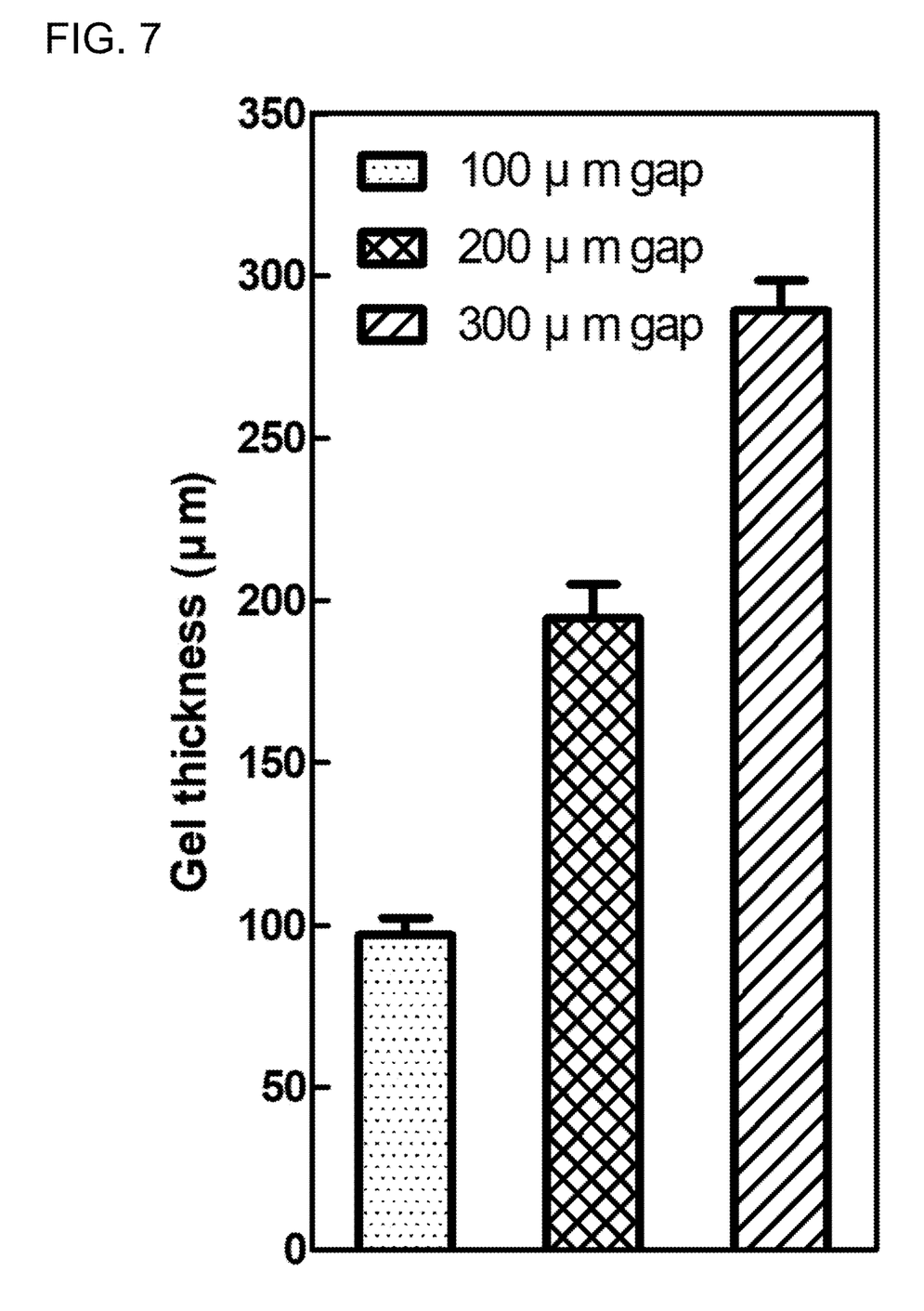
FIG. 7 shows that the thickness of a hydrogel can be precisely adjusted using a thickness adjustment unit.

Moreover, to confirm a thickness adjustment effect of the thickness adjustment apparatus, when the thickness adjustment apparatus was installed in the bezel unit, it was spaced a distance of 100 μm, 200 μm or 300 μm from the bottom surface and then UV was applied, thereby solidifying the PEGDA. As a result, as shown in FIG. 7, it was confirmed that the PEGDA film was able to be formed to a desired thickness by the thickness adjustment apparatus.

Figure 8:
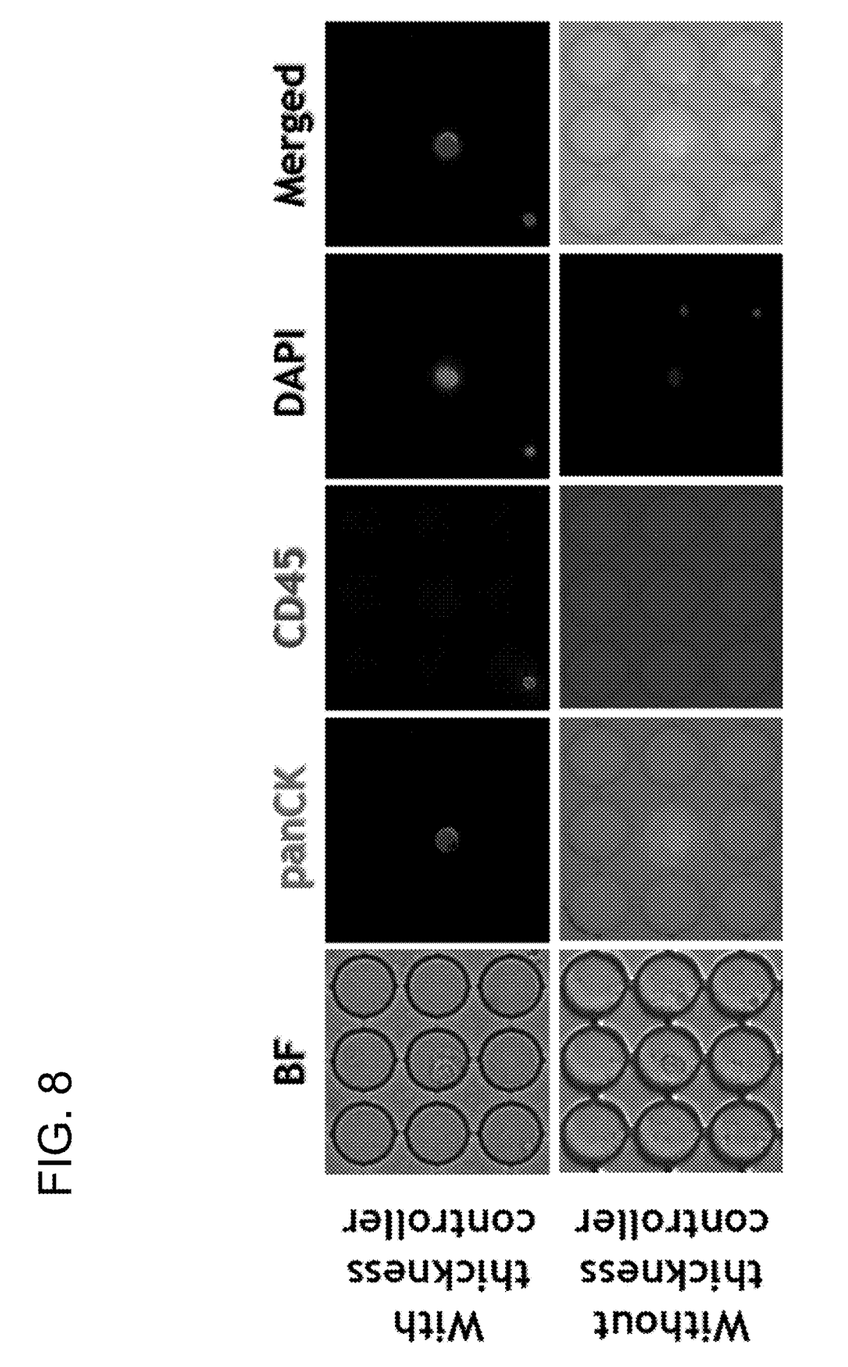
FIG. 8 shows the result of cell staining according to one embodiment of the present disclosure.

Example 2. Result of Cell Staining According to the Presence or Absence of Thickness Adjustment Apparatus To confirm a staining quality according to the thickness of the PEGDA film, degrees of staining of Bright field (BF), panCK, CD45 and DAPI were compared according to the presence or absence of the thickness adjustment apparatus. As a result, when there was no thickness adjustment apparatus, under the BF condition, it was confirmed that there was no significant change or a somewhat faint image was obtained, and there was a very significant difference in fluorescence imaging. Due to the difficult cell delivery of a reagent or a non-efficient washing process because of the unadjusted thickness of a hydrogel, it was confirmed that, in the case of staining signals such as panCK and CD45, cell staining qualities are poor compared to when there is a thickness adjustment apparatus under all conditions, for example, background signals are very strongly shown under the same imaging conditions (FIG. 8).

Example 3. Effect of Improving Cell Loss Rate

Figure 9:
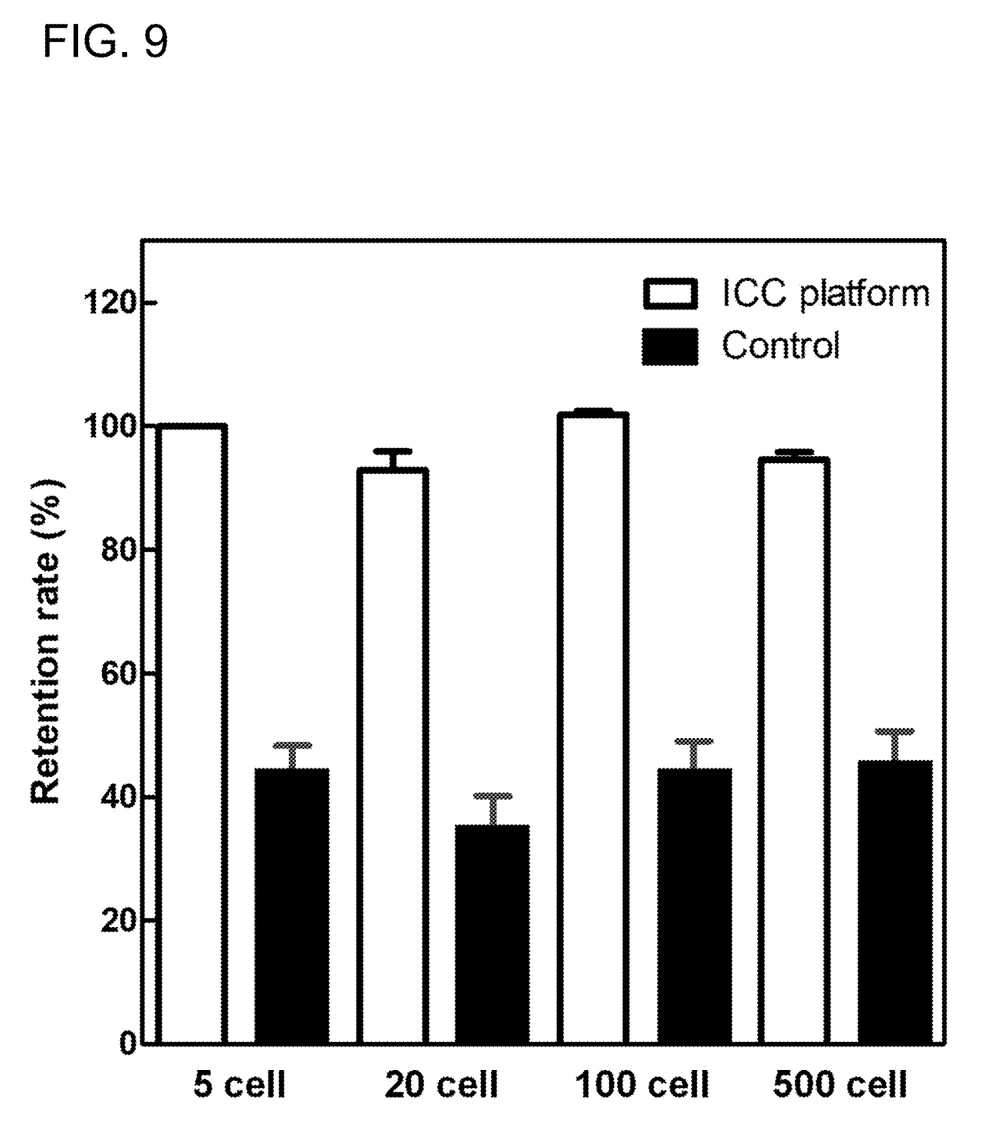
FIG. 9 shows a cell loss rate after cell staining.

To confirm cell loss when ICC was performed using an apparatus for cell staining without cell loss of the present disclosure, cell retention rates when ICC was performed using a conventional ICC protocol that had been used for non-adhesion cells, and ICC was performed using the apparatus of the present disclosure were compared. Specifically, when 5, 20, 100, or 500 cells were loaded, in all cases, the conventional protocol exhibited a cell retention rate of 50% or less, whereas the method of the present disclosure exhibited a cell retention rate of 90% or more. Therefore, according to the method of the present disclosure, it was confirmed that the retention rates were remarkably high (FIG. 9).

In addition, when staining before and after ICC was compared in one section, it was confirmed that, before ICC, the luminescence of CD45 was confirmed, and after ICC, the luminescence of panCK was confirmed at the same spot, thereby proving the precision of the present disclosure. Afterward, the initial cell numbers, the cell numbers before ICC, the cell numbers after ICC when the platform of the present disclosure and the conventional ICC protocol were used were counted to compare cell loss. When the platform of the present disclosure was used, in all cases of the initial cell numbers, a retention rate was 95% or more, and particularly, except the case of 20 cells, a retention rate was 99.9% or more, proving that the present disclosure exhibited an excellent cell retention rate.

Example 4. Effect of Isolating Single Cells

After ICC was performed using the apparatus for cell staining without cell loss of the present disclosure, cell picking was attempted to isolate single cells. For successful cell picking, a suitable hardness of a hydrogel is important. This is because, if the hydrogel is too hard, it is difficult for a pipette for cell picking to pass through the gel, and the collection position is distorted depending on the degree of rigidity in some cases. For the PEGDA used in the present disclosure, a concentration of 10% to 50% was preferred, and a physical property value between 500 Pa to 10 MPa was preferred.

Figure 11:
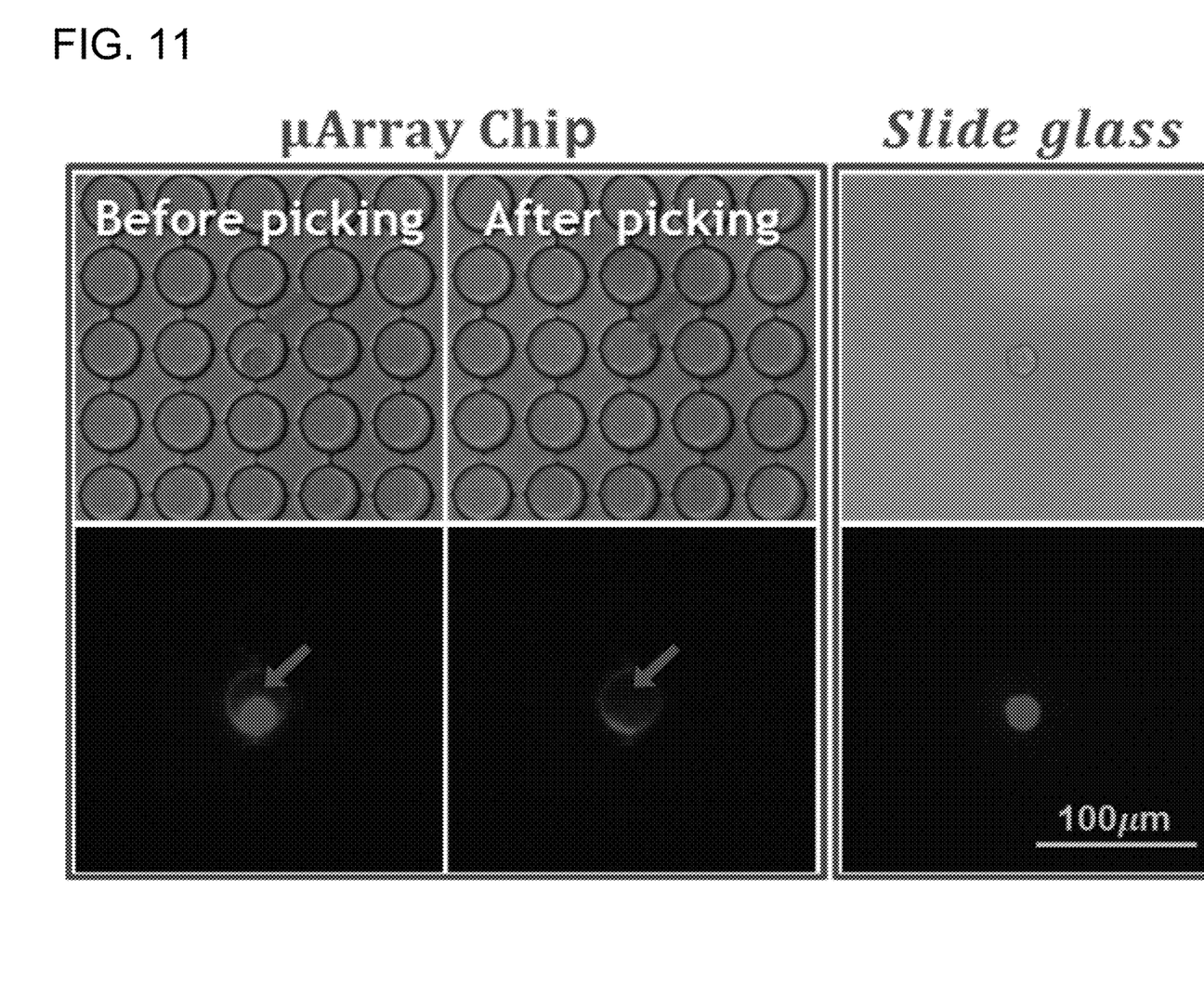
FIG. 11 shows a result of single cell isolation according to one embodiment of the present disclosure.

In one embodiment of the present disclosure, 20% PEGDA was used, and the pipette was able to successfully isolate single cells through the hydrogel. Generally, when single cells are isolated using a pipette, a fluid flow is generated while the pipette essentially moves to isolate cells, and thus the location of cells may change. However, in the method of the present disclosure, since the cells are immobilized in the hydrogel, there is no change in the location of cells due to the movement of the pipette, confirming an effect of more precise isolation of single cells (FIG. 11).

A method for cell staining without cell loss according to the present disclosure can effectively prevent cell loss during staining and analysis of rare cells that are becoming important in clinical diagnosis, and thus can facilitate observation, analysis and diagnosis thereby even with a trace amount of samples.

In addition, as the method for cell staining without cell loss according to the present disclosure allows immobilization of cells, it makes discrimination and isolation of single cells easy, and can be effectively used in analysis of the isolated cells.

It will be apparent to those skilled in the art that various modifications can be made to the above-described exemplary embodiments of the present disclosure without departing from the spirit or scope of the invention. Thus, it is intended that the present disclosure covers all such modifications provided they come within the scope of the appended claims and their equivalents.

What is claimed is:

1. A method for cell staining without cell loss, comprising:
    (a) inputting a phase change material and a biosample containing cells to be analyzed into a chamber;
    (b) localizing the cells to be analyzed, which are suspended in the biosample, on a bottom surface of the chamber;
    (c) inserting a thickness adjustment unit into the chamber such that a bottom surface of the thickness adjustment unit is positioned above the bottom surface of the chamber, forming a space between the bottom surface of the thickness adjustment unit and the bottom surface of the chamber;
    (d) immobilizing the cells on the bottom surface of the chamber by solidifying the phase change material;
    (e) removing the thickness adjustment unit from the chamber; and
    (f) staining the immobilized cells,
    wherein after the step of (e), the solidified phase change material is formed in a thickness of 300 µm or less in the space between the bottom surface of the thickness adjustment unit and the bottom surface of the chamber throughout an entire chamber, and
    wherein the phase change material is a photocurable material or heat-curable material.

2. The method of claim 1, wherein the phase change material and the biosample in the step (a) are input simultaneously, in combination or independently.

3. The method of claim 1, wherein the phase change material is a photocurable hydrogel or heat-curable hydrogel.

4. The method of claim 1, wherein the phase change material includes one or more materials selected from the group consisting of polyethylene glycol (PEG) acrylate derivatives, PEG methacrylate derivatives, polyvinyl alcohol (PVA) derivatives, hyaluronic acid derivatives, dextran methacrylate, poly(N-isopropylacrylamide) (pNiPAAm), polyethylene glycol (PEG), poly(propylene glycol) (PPG), poly(methacrylic acid) (PMAA), methylcellulose (MC), chitosan, and poloxamers.

5. The method of claim 1, wherein the phase change material is poly ethylene glycol diacrylate (PEGDA).

6. The method of claim 1, wherein the biosample is one or more selected from the group consisting of a cell sample, a cell culture medium, a tissue extract, cancer tissue, serum, plasma, saliva, tears, sweat, urine, feces, a cerebrospinal fluid (CSF), ascites, an amniotic fluid, semen, and milk.

7. The method of claim 1, wherein, in the step (b), the cells are localized on the bottom surface of the chamber using a centrifugal force.

8. A method for analyzing a single cell, comprising:
    (a) inputting a phase change material and a biosample containing cells to be analyzed into a chamber;
    (b) localizing the cells to be analyzed, which are suspended in the biosample, on a bottom surface of the chamber;
    (c) inserting a thickness adjustment unit into the chamber such that the bottom surface of the thickness adjustment unit is positioned above the bottom surface of the chamber, forming a space between the bottom surface of the thickness adjustment unit and the bottom surface of the chamber;
    (d) immobilizing the cells on the bottom surface by solidifying the phase change material;
    (e) removing the thickness adjustment unit from the chamber;
    (f) staining the immobilized cells; and
    (g) isolating the stained cells,
    wherein after the step of (e), the solidified phase change material is formed in a thickness of 300 µm or less in the space between the bottom surface of the thickness adjustment unit and the bottom surface of the chamber throughout an entire chamber, and
    wherein the phase change material is a photocurable material or heat-curable material.

* * * * *